United States Patent [19]

Sarstedt

[11] 4,378,812
[45] Apr. 5, 1983

[54] DEVICES FOR SAMPLING BLOOD

[75] Inventor: Walter Sarstedt, Nümbrecht, Fed. Rep. of Germany

[73] Assignee: Kunststoff-Spritzgubwerk, Nümbrecht, Fed. Rep. of Germany

[21] Appl. No.: 212,151

[22] Filed: Dec. 2, 1980

[30] Foreign Application Priority Data

Dec. 4, 1979 [DE] Fed. Rep. of Germany ....... 2948653

[51] Int. Cl.³ ............................................... A61M 5/00
[52] U.S. Cl. ..................................... 128/765; 128/766
[58] Field of Search .............. 128/763, 764, 765, 215, 128/218 N, 232, 234

[56] References Cited

U.S. PATENT DOCUMENTS

| 3,494,351 | 2/1970 | Horn | 128/762 |
| 3,585,984 | 6/1971 | Buchanan | 128/764 |
| 3,930,492 | 1/1976 | Hatsuno et al. | 128/765 |
| 3,985,122 | 10/1976 | Gopham | 128/765 |
| 4,216,782 | 8/1980 | Sarstedt | 128/765 |
| 4,240,425 | 12/1980 | Akhavi | 128/218 N |

Primary Examiner—Kyle L. Howell
Assistant Examiner—Nancy A. B. Swisher
Attorney, Agent, or Firm—Townsend and Townsend

[57] ABSTRACT

A blood-sampling device consisting of a cylindrical tube with a plunger therein, which is closed by an elastomeric stopper which can be pierced by the rear end of a two-ended cannula, the other end of which is intended to be introduced into a vein, whereas the cannula is disposed within a tubular guide sleeve which can be pushed over the front end of the cylindrical tube.

13 Claims, 8 Drawing Figures

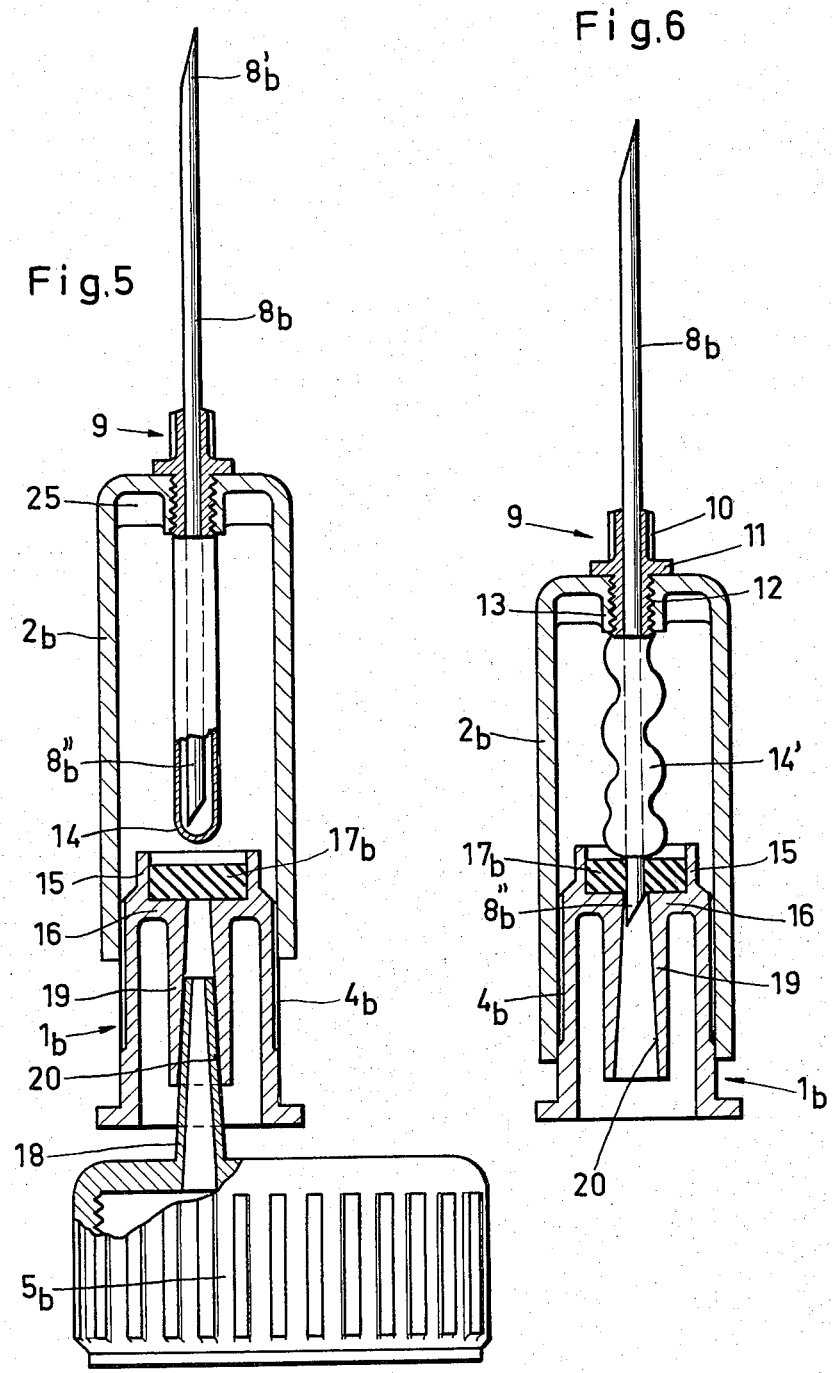

DEVICES FOR SAMPLING BLOOD

The invention relates to a blood-sampling device, consisting of a cylindrical sampling tubule having a piston, which is displaceable therein in an air-tight manner, and a closing plug which can be pierced, at the front end as well as tubular guide sleeve which can be pushed over this front end of the sampling tubule and the front end of which carries a two-ended cannula which is sharpened on both sides and of which the front end projecting from the guide sleeve is intended to be introduced into a vein, whilst its rear end projecting into the guide sleeve serves to pierce the closing plug when the guide sleeve is pushed further onto the front end of the sampling tubule.

A blood-sampling device of the type described above has been disclosed by U.S. Pat. No. 3,930,492. This known blood-sampling device is intended, in particular, to prevent the blood collected from coming into contact with atmospheric air, since otherwise the results of certain investigations would be falsified. In the known blood-sampling device, the guide sleeve is directly pushed over the sampling tubule, the external shape of which is cylindrical. The central position of the cannula, necessarily resulting from this, makes it difficult to handle, in particular in the case of sampling tubules of relatively large diameter, which are intended for greater volumes of blood. An eccentric position of the cannula, as is otherwise known from simple blood-sampling devices, cannot be provided in this known device with a two-ended cannula and a closing plug which can be pierced. Moreover, the subsequent removal of the blood sample from the sampling tubule is possible only by expelling the blood by means of renewed introduction of a piercing cannula into the closing plug and pushing the piston forward.

If, on the other hand, it were desired in the known device to remove the closing plug from the sampling tubule, parts of the blood sample are necessarily sprayed around in the form of very fine droplets, so that clean and sterile working in this way would not be possible.

It is the object of the invention to develop the known blood-sampling device further in such a way that convenient and clean working during the blood-sampling and during the subsequent further processing of the blood sample which has been taken is possible.

According to the invention, this object is achieved when the front end of the sampling tubule is formed by a closing cap with a cylindrical extension which axially projects from the latter and carries the closing plug which can be pierced, and when the guide sleeve which can be pushed over this extension and carries the two-ended cannula is provided with a vent.

Compared with the known device, the provision of a closing cap on the device has the advantage that, after the blood sample has been taken, the sampling tubule can be opened by simply taking off this closing cap and the blood sample, or parts thereof, can then be removed in any desired manner. It would not be possible to fit such a closing cap on the known device, since there would then no longer be any secure guiding of the guide sleeve.

The closing cap is either screwed onto the front end of the sampling tubule or it is just simply pushed on.

Venting of the guide sleeve, which in principle can be carried out at almost any desired point thereof, prevents the formation of a positive pressure in the guide sleeve when it is pushed back.

The device according to the invention also makes it possible in a simple manner to arrange a closure, known per se, for the rear end of the two-ended cannula and thus, during a change of the sampling tubule, to close the cannula, the front end of which remains in the vein. For this purpose, a piece of thin tubing of a soft-elastic material, closed at its end, is drawn over the rear end of the cannula. When the guide sleeve is pushed back onto the extension of the closing cap, the sharpened rear end of the cannula first pierces the rear end of this thin tubing and then pierces the closing plug in the extension. During this, the tubing itself is compressed like a concertina. When the extension is then pulled out of the guide sleeve again, after the connected sampling tubule has been filled, the tubing is extended again and the pierced lower end of the tubing recloses and thus seals the rear end of the cannula.

Preferably, provision is made here for the adhesion between the guide sleeve and the extension to be only just sufficiently strong to prevent the guide sleeve from being pushed off the extension by the compressed tubing. This ensures that the guide sleeve which has been pushed back remains in its position until it is pushed off again by hand.

Preferably, provision is made for the axially projecting extension to be arranged eccentrically to the closing cap. This considerably facilitates the sampling of blood, in particular in the case of relatively large sampling tubules.

Preferably, the external diameter of the guide sleeve and the eccentricity of the extension provided here are such that the guide sleeve does not radially project beyond the circumference of the closing cap. This ensures that the blood-sampling device can be smoothly placed on the forearm of the patient or another point, from where blood is to be taken.

The inner shell surface of the guide sleeve is either of circular-cylindrical form, in which case the desired friction between the guide sleeve and the extension can readily be predetermined, as will be explained in more detail below; alternatively, however, the inner shell surface of the guide sleeve can also be slightly widened conically towards the aperture. In this case, however, the cone angle is preferably arranged to be so small that the tip at the rear end of the cannula reliably runs into the free passage bore located under the closing plug, when the guide sleeve is pushed on.

The reason is that, if the inner shell of the guide sleeve and the outer shell of the extension in the said conical design are not yet fully pushed together, there is not only a certain radial play between these two parts, but correspondingly there is also a possibility of the guide sleeve being twisted relative to the extension. If the cone angle is too large and hence the play is unduly extensive, this twisting could reach such an extent that the rear end of the cannula, instead of running into the free space located below, when the closing plug is pierced, strikes a solid wall somewhere and thus prevents the guide sleeve from being pushed back further.

In order to enable the adhesion between the guide sleeve and the extension to be readily predetermined in every case, it is proposed to provide at least three guide ribs which are distributed over the circumference of the extension, run parallel to the axis and project radially beyond the shell surface of the extension. In this way, improved guiding and well-defined adhesion are achieved at the same time.

Incidentally, a blood-sampling device with a two-ended cannula and a closing plug, which can be pierced, on the sampling tubule has already been disclosed by German Auslegeschrift No. 1,812,742 for the case of sampling tubules without a piston. In this device, the reduced pressure for drawing the blood through the cannula is not generated by a piston which can be retracted, but is a priori present in the sampling tubule. This known device also has the disadvantages discussed at the outset and, additionally, it has the known disadvantages of the piston-less blood-sampling devices, in particular the occasionally occurring ingress of air into the evacuated sampling tubule, and further disadvantages which, however, are of no interest in this context.

The advantages of the blood-sampling device according to the invention manifest themselves in its mode of action:

The closed sampling tubule which, under certain circumstances, contains a small amount of a specific reagent in the solid or liquid form, is taken from the pack and a likewise taken sterile guide sleeve with a cannula is pushed over the extension of the closing cap of the sampling tubule. After the guide sleeve has initially been pushed onto the extension only to such an extent that it is firmly and securely guided by the latter, the front free end of the cannula is then introduced into the vein, while firmly holding the guide sleeve with the thumb and index finger. Whilst retaining the position of the guide sleeve and the cannula, the sampling tubule with its extension is then moved forward. The rear end of the cannula, located in the guide sleeve, thus pierces the closing plug and then, via the cannula, makes a connection between the vein and the interior of the sampling tubule. Only now, once all the parts are in their correct position, the piston is slowly retracted, mechanically or pneumatically, depending on its construction, and the blood sample is thus taken in a gentle manner.

If the guide ribs, described above, on the extension are not provided, preferably at least one groove which extends through the outer shell of the extension in the direction parallel to the axis is provided for the purpose of venting the guide sleeve when the latter is pushed on.

The closing plug which can be pierced is advantageously inserted into the front end of the extension and preferably represents a thin disc which is secured by inward-pointing lugs on the extension against being pressed through.

Preferably, a foil which additionally closes the passage is also located under the closing plug. This measure is appropriately taken whenever a chemical reagent is to be contained in the sampling tubule, which reagent could, on prolonged storage, attack, for example incipiently dissolve or swell, the closing plug consisting of a soft-elastic material. In such a case, the foil protects the underside of the closing plug from damage of this kind. In use, the foil is then pierced like the closing plug itself by the rear end of the cannula. Whilst, when the cannula is subsequently withdrawn from the plug, the latter will reclose in the known manner, the thin foil will of course no longer ensure a safe seal. Since, however, the blood sample which has been taken is soon processed, this is no longer necessary.

Moreover, the closing plug is inserted into the extension under a radial pre-tension and is advantageously held securely by an inward-flanged upper edge of the extension. Due to this radial pre-tension, the safe closure of the pierced orifice, after the cannula has been withdrawn, is further improved. The inward-flanged upper edge of the extension ensures that the closing plug is not also withdrawn inadvertently, when the cannula is withdrawn. Advantageously, the above-mentioned foil can also be formed integrally with the extension.

Instead of the flange on the upper edge of the collar on the extension, a rigid holding disc which is provided with a central bore and which is placed on the disc-shaped closing plug and is firmly joined to the upper edge of the extension, can preferably also be used.

The cannula can be irreleasably inserted into the guide sleeve and thrown away together with the latter after use. This guide sleeve allows simple handling and, due to its small size, is also very cheap to manufacture, so that its re-use is not absolutely necessary.

In another embodiment, however, the cannula can also be inserted into a holder provided with an external thread and can be screwed, together with the holder, into a neck, provided with a threaded bore, in the guide sleeve. In such a case, it would be possible under certain circumstances to re-use the guide sleeve, after the holder with the cannula has been unscrewed.

Preferably, the extension is integrally joined to the closing cap. It is also possible, however, to start with a known blood-sampling device, that is to say a cylindrical sampling tubule having a piston, which is displaceable therein, a closing cap which is screwed on, and a connecting cone, projecting from the latter, for placing cannulas thereon, and then to design the extension as a special adaptor between such a device and the guide sleeve. In such a design, the extension has, underneath the closing plug, a tube branch with a conical bore, by means of which it can be placed onto the connecting cone of the closing cap of any known blood-sampling device.

In the following text, the invention is explained in more detail in illustrative embodiments by reference to the drawing in which:

FIG. 5 shows a section through another illustrative embodiment of the invention;

FIG. 6 shows a section through the device shown in FIG. 5, after the closing plug has been pierced;

Figure 1:
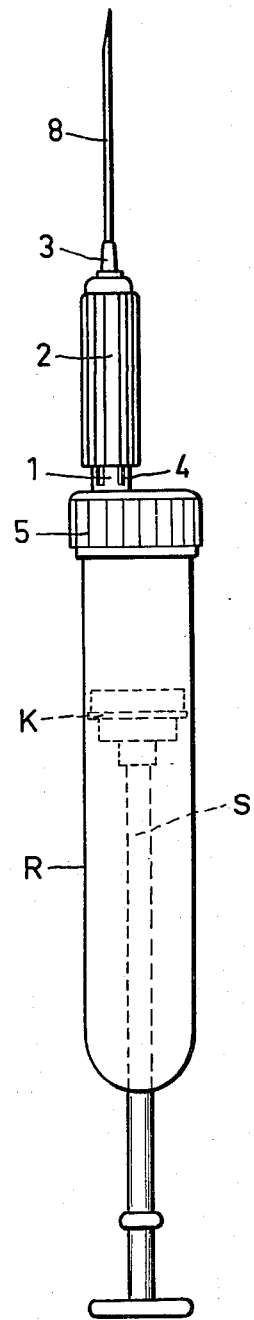
FIG. 1 shows a side view of a blood-sampling device according to the invention.
Figure 2:
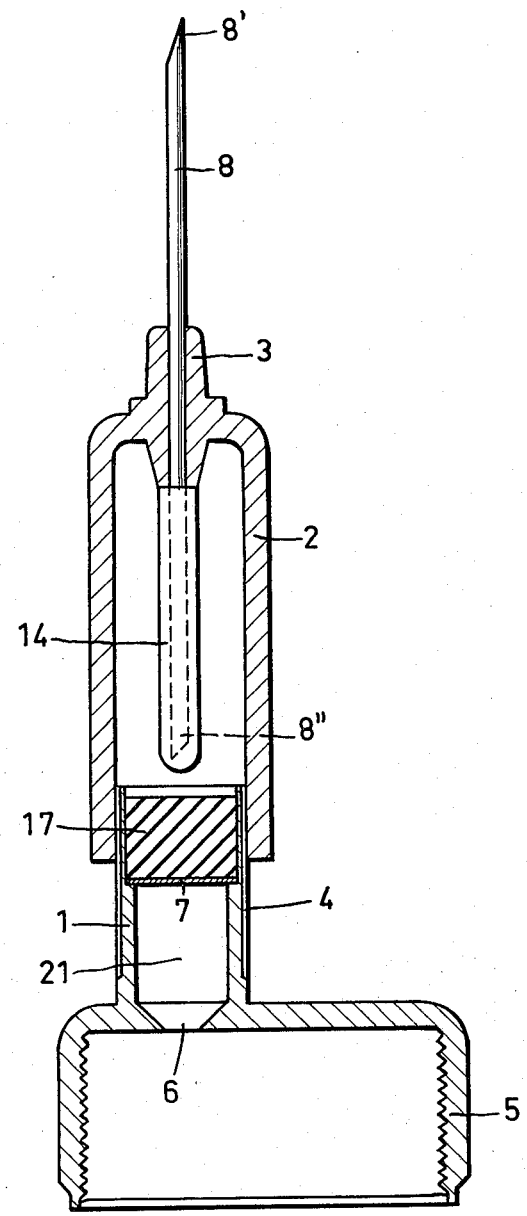
FIG. 2 shows a section through the extension and guide sleeve of the blood-sampling device in FIG. 1, but on an enlarged scale.

The blood-sampling device shown in FIGS. 1 and 2 consists of a cylindrical sampling tubule R with a piston K, which is displaceable therein in an air-tight manner and has a piston rod S, of a closing cap 5 which is screwed onto an external thread of the sampling tubule R, and of a guide sleeve 2 which is pushed over an extension 1 of the closing cap 5 and which carries a two-ended cannula 8 in a branch 3. Both the closing cap 5 with the extension 1 and the guide sleeve 2 with the branch 3 consist of a thermoplastic. The front end 8' and the rear end 8" of the cannula 8 are sharpened and a piece of soft rubber tubing 14 closed on the underside is drawn over the rear part, projecting into the guide sleeve 2, of the cannula 8 so that its rear part is closed.

Eccentrically to its central axis, the closing cap has a narrow passage 6 which widens upwards like a funnel and merges into the cylindrical interior 21 of an extension 1 which adjoins the upper side of the closing cap 5. In its upper part, the interior 21 widens and receives there a soft rubber closing plug 17 which has been inserted with a radial pre-tension into the extension 1. One or more grooves 4 which run parallel to the axis and serve for venting extend through the outer shell surface of the extension 1.

After the front end 8' of the cannula has been introduced into the vein, the guide sleeve 2 is held firmly relative to the body of the patient, whilst the sampling tubule R with its closing cap 5 and the extension 1 projecting therefrom is pushed forward in the direction of the guide sleeve 2. During this, the rear end 8" of the cannula first pierces the lower end of the rubber tubing 14 and then the closing plug 17. As can be seen in FIG. 6, relating to another embodiment, this tubing is thus compressed like a concertina.

Underneath the closing plug 17, a plastic foil 7 is located which is likewise pierced by the rear end 8" of the cannula when the two parts are pushed together.

In this position, the piston K is retracted. As a consequence, blood flows from the vein through the cannula 8 into the interior 21 of the extension 1 and from there into the sampling tubule.

After sampling has taken place, the entire device is then taken off, the front end 8' of the cannula being removed from the vein. The guide sleeve with the cannula is then drawn off the extension and thrown away. Due to its radial pre-tension, the closing plug 17 recloses and the blood sample is safely stored in the sampling tubule R.

If, however, it is desired to fill a second or third sampling tubule with blood from the same patient, the front end 8' of the cannula is left in the vein, that is to say the guide sleeve 2 is firmly held on the body of the patient, and merely the sampling tubule is removed together with the closing cap 5 and the extension 1. During this, the closing plug 17 closes, as does the tubing 14 which thus seals the rear end 8" of the cannula. A second, empty sampling tubule R with a screwed-on closing cap 5 can now be put in place and, with its extension 1, inserted into the guide sleeve 2.

Figure 3:
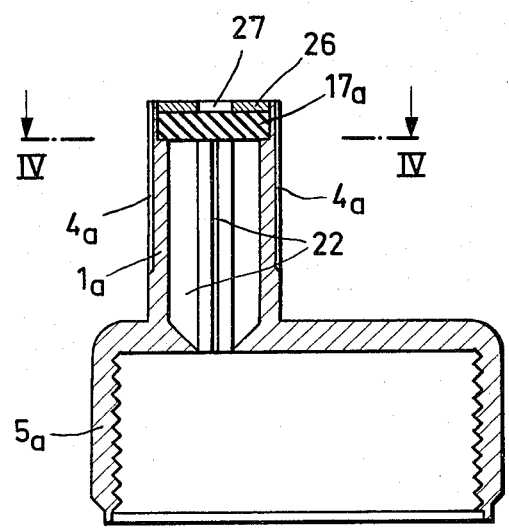
FIG. 3 shows a section, similar to that in FIG. 2, through a closing cap with an extension, in a different design.
Figure 4:
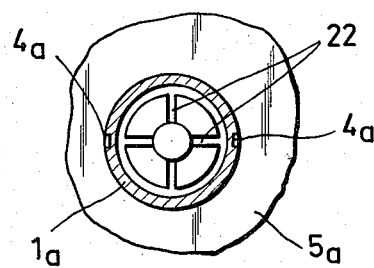
FIG. 4 shows a section along the line IV—IV in FIG. 3.

In the modified embodiment of the closing cap 5a with the extension 1a, as shown in FIG. 3, a closing plug 17a in the form of a thin soft rubber disc is used. To support this soft rubber disc against inadmissible flexure, four wings 22 are provided which project radially inwards from the extension 1a, as can be seen particularly in FIG. 4. In the centre of the extension 1a, these wings leave a narrow cylindrical free space into which the rear end of the cannula can enter. The outer shell of the extension 1a is provided with longitudinal grooves 4a which effect venting when the extension is inserted into the associated guide sleeve 2.

A rigid disc 26 with a central bore 27 is placed on the closing plug 17a, which rigid disc consists, like the closing cap 5a and the extension 1a, of plastic and which, after insertion, is firmly joined to the upper edge of the extension 1a, so that, during piercing and subsequent withdrawal of a cannula, there is no risk of the disc-shaped closing plug 17a being pulled out of the extension 1a.

Compared with the embodiments described above, the blood-sampling device according to FIGS. 5 and 6 is modified in such a way that it can be used in conjunction with known sampling devices, for example injection syringes, having a conical connecting branch. As indicated in FIG. 5, a conical connecting branch 18 which is usually provided for fitting the conical connecting funnel of a cannula, is located on the closing cap 5b of such a known device. In place of such a connecting funnel, the separately formed extension 1b is pushed on in this case, and in particular by means of a tube branch 19 which projects from the upper transverse wall 16 of the extension and extends into the interior thereof and has a conical bore 20 which fits the conical connecting branch 18. A narrowed collar 15, into which a thin soft rubber disc is inserted as a closing plug 17b, projects upwards from the transverse wall 16 of the extension 1b. The outer shell of the extension 1b is provided with longitudinal grooves 4b which effect venting when the extension is inserted into the associated guide sleeve 2b.

The guide sleeve 2b is closed at its upper end and carries there a receding neck 13 with an internal thread into which a special cannula holder 9 is screwed by its external thread 12. Screwing-in is facilitated by longitudinal ribs 10 and limited by a flange 11 which comes to rest on the upper end wall of the guide sleeve 2b. For reinforcement, there are radial ribs 25 between the neck 13 and the shell of the guide sleeve 2b.

The cannula 8b, inserted in the holder 9, is introduced with its front end 8b' into the vein or the like. A piece of soft rubber tubing 14 is drawn over the rear end 8b" and closes the latter. When the guide sleeve 2b is displaced relative to the collar 1b into the position shown in FIG. 6, this tubing is pierced by the rear end 8b" of the cannula and is deformed like a concertina, as shown at item 14' in FIG. 6.

When the guide sleeve 2b and the extension 1b are drawn apart again, the tubing 14 is re-extended into its position shown in FIG. 5 and closes the rear end 8b" of the cannula.

Figure 7:
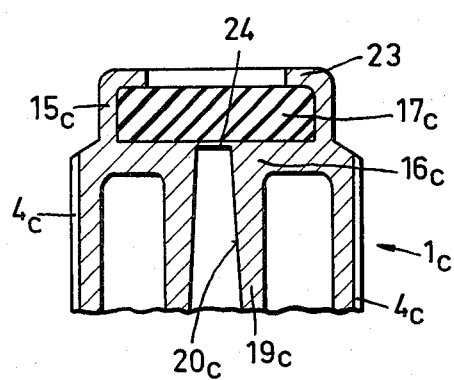
FIG. 7 shows a part section through another embodiment of the extension.

In the modified embodiment according to FIG. 7, the upper edge 15c of the extension 1c is bent over radially inwards at 23 and thus firmly holds the closing plug 17c in its position.

The upper end of the conical bore 20c of the tube branch 19c is here closed by a foil 24 which was integrally injection-moulded during the manufacture of the extension 1c from thermoplastic. Longitudinal grooves 4c are also provided in this case on the outer shell of the extension 1c.

Figure 8:
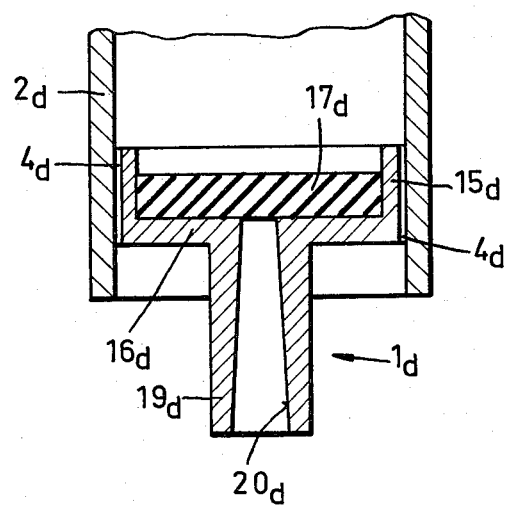
FIG. 8 shows a part section through a further embodiment of the extension, after insertion into the lower end of the guide sleeve.

FIG. 8 showed a further embodiment of the extension 1d, inserted into the lower end of the guide sleeve 2d. To receive the closing plug 17d, merely a short cylinder 15d is provided here, which has external longitudinal grooves 4d and is closed on the underside by an end wall 16d. This end wall with a central bore is then again adjoined downwards by a tube branch 19d with a conical bore 20d.

I claim:
1. A blood sampling device comprising:
    a cylindrical sampling tubule having front and rear ends;
    a piston displacable in air tight manner in said sampling tubule;

a closure cap having a circumference, said closure cap being removably fitted to said front end of said cylindrical sampling tubule;

an axially projecting tubular extension provided on said cap;

a passage in said closure cap in communication with said extension;

a piercable, self-sealing closure plug inserted in said extension;

a guide sleeve having a diameter with an open end and a closed end, said guide sleeve being axially movable on said extension, a space separating a portion of said guide sleeve from said closure cap;

a cannula having sharpened front and rear ends mounted in the closed end of said guide sleeve and axially aligned with said guide sleeve, said sharpened front end projecting forwardly from said guide sleeve for introduction into a patient and said sharpened rear end projecting rearwardly into said guide sleeve so that it can puncture said closure plug during relative axial movement between said guide sleeve and said extension; and means for venting the space between said guide sleeve and said extension.

2. A device according to claim 1, wherein said extension is eccentrically positioned on said cap.

3. A device according to claim 1, further comprising: a tubular sheath, said sheath being closed at its rear end and positioned over said sharpened rear end of the cannula, wherein said tubular sheath is pierced by said sharpened rear end when the guide sleeve is pushed back, and is then compressed like a concertina, and wherein said guide sleeve is an interference fit on said extension with the cohesion between the guide sleeve and the extension being only just sufficiently strong to prevent the guide sleeve from being pushed off the extension by the compressed tubular sheath.

4. A device according to claim 2, wherein the external diameter of the guide sleeve and the eccentric position of said extension on said closure cap are selected so that the guide sleeve does not project radially beyond the circumference of the closure cap.

5. A device according to claim 1, wherein said guide sleeve has an inner surface of right-cylindrical form.

6. A device according to claim 1, further comprising:
an aperture adjacent said sharpened rear end of the cannula, wherein said guide sleeve has an inner surface terminating at said aperture and wherein said inner surface diverges conically at a cone angle towards the aperture.

7. A device according to claim 6, wherein said cone angle is such that said sharpened rear end reliably enters said passage in said closure cap beneath said closure plug following piercing of the same.

8. A device according to claim 1, wherein at least three axially extending and radially projecting guide ribs are distributed around said extension.

9. A device according to claim 1, wherein said means for venting the space between said guide sleeve and said extension comprises at least one axially extending groove in said extension.

10. A device according to claim 1, wherein said extension has front and rear ends and said closure plug is inserted into said front end.

11. A device according to claim 1, further comprising:
said closure plug having front and rear sides; and
a foil located at said rear side of said closure plug.

12. A device according to claim 1, wherein said cannula is irreleasably inserted into said guide sleeve.

13. A device according to claim 1, wherein said extension is integrally joined to said closure cap.

* * * * *